(12) United States Patent
Jannot

(10) Patent No.: US 7,303,568 B2
(45) Date of Patent: Dec. 4, 2007

(54) SUTURE AND CLAMP RETAINER AND ORGANIZER

(76) Inventor: Paul R. Jannot, 7535 Chant Ct., Lewis Center, OH (US) 43035

( * ) Notice: Subject to any disclaimer, the term of this patent is extended or adjusted under 35 U.S.C. 154(b) by 571 days.

(21) Appl. No.: 10/627,364

(22) Filed: Jul. 25, 2003

(65) Prior Publication Data

US 2004/0073233 A1    Apr. 15, 2004

(51) Int. Cl.
 *A61B 17/04* (2006.01)
(52) U.S. Cl. .................................................. 606/148
(58) Field of Classification Search ................ 606/148; 206/370
See application file for complete search history.

(56) References Cited

U.S. PATENT DOCUMENTS

| | | | | |
|---|---|---|---|---|
| 2,591,805 A | * | 4/1952 | Gossett | 211/89.01 |
| 2,692,599 A | * | 10/1954 | Creelman | 606/148 |
| 3,515,129 A | * | 6/1970 | Truhan | 600/206 |
| 3,696,920 A | * | 10/1972 | Lahay | 206/370 |
| 4,185,636 A | * | 1/1980 | Gabbay et al. | 606/148 |
| 4,274,398 A | * | 6/1981 | Scott, Jr. | 600/233 |
| 4,492,229 A | | 1/1985 | Grunwald | 128/303 |
| 5,207,703 A | * | 5/1993 | Jain | 606/232 |
| 2003/0055439 A1 | * | 3/2003 | Koseki | 606/148 |

* cited by examiner

*Primary Examiner*—(Jackie) Tan-Uyen Ho
*Assistant Examiner*—Melanie Tyson

(57) ABSTRACT

A suture clamp and/or suture retainer and organizer device for use during a surgical procedure, including an elongated body formed of resilient material and has a plurality of spaced lateral slits through one surface. The slits are individually identified and are sized to receive and grip a surgical suture. A tapered pocket is located adjacent to and opens into each slit for receiving and retaining the nose of a hemostat attached to a suture. The device may be attached by adhesive backing or by clamps to a surgical drape or other support surface.

7 Claims, 5 Drawing Sheets

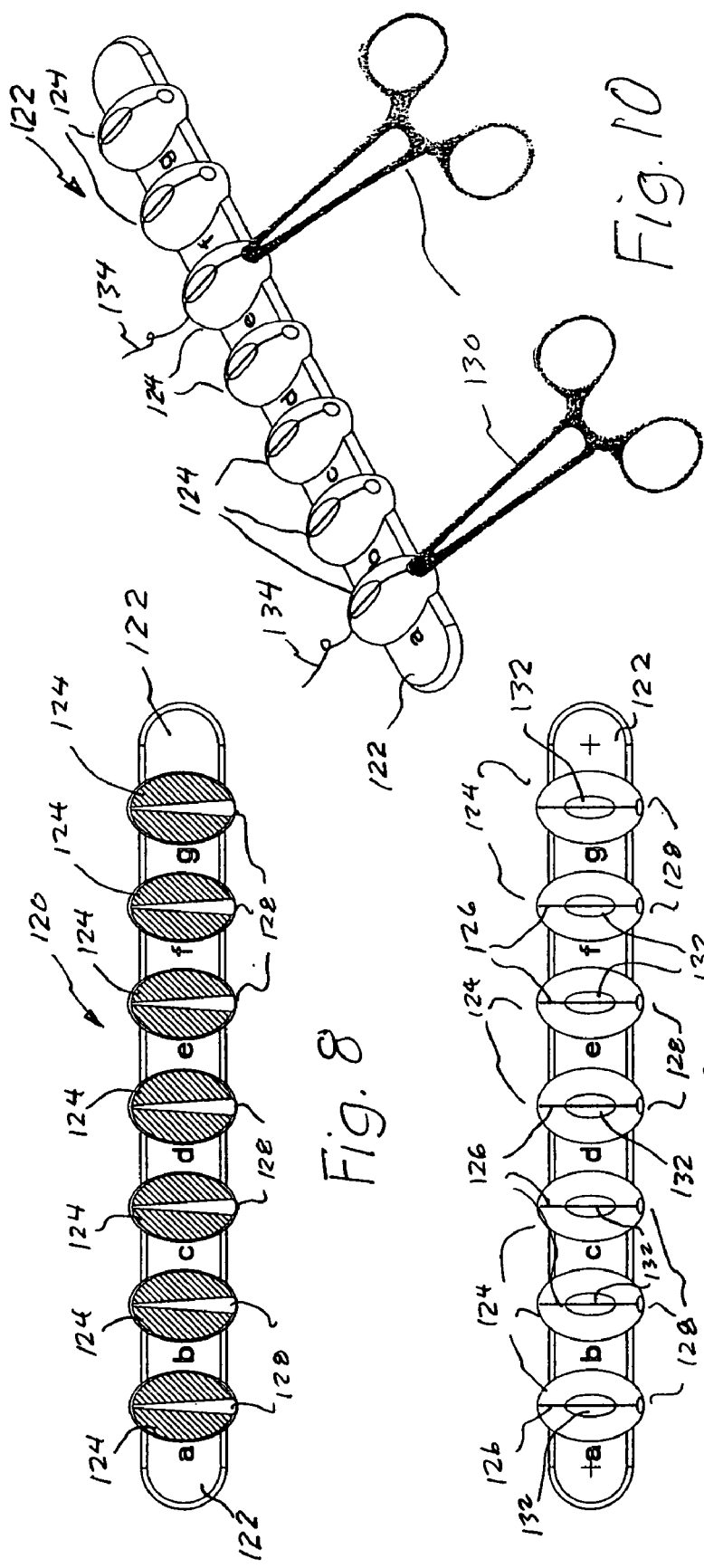

SUTURE AND CLAMP RETAINER AND ORGANIZER

TECHNICAL FIELD

This invention relates to devices used in aid of surgery and, more particularly, to a device for holding suture clamps and/or sutures and for organizing sutures during surgery.

BACKGROUND OF THE INVENTION

Many kinds of surgery require the use of multiple sutures that are used to pull severed muscles, nerves and tendons away from the surgery site. One of these surgeries is heart surgery, where multiple sutures are used to repair the mitral vessels. If the sutures are not properly organized, they become tangled and complicate the surgeon's job. To aid the heart surgeon, many suture organizers have been developed, the most common of which is known as the Gabbay-Frater organizer. Examples of this type of device are shown in U.S. Pat. No. 4,185,636—Gabbay, and U.S. Pat. No. 4,492,229—Grunwald. These heart surgery suture organizers are specific to heart surgery, where the patient is supine and motionless.

Another suture organizer, designed for hysterectomies is disclosed in U.S. Pat. No. 2,692,599, which is also useful when the patient is supine and motionless. In these surgeries, gravity is often used to tension the sutures, thus necessitating a motionless surgery site. However, in orthopedic surgeries where ligation of soft tissue, such as muscles, tendons and nerves is necessary, the patient is not supine and the surgery site is not motionless.

These surgeries include joint surgeries, such as common rotator cuff repair surgery. Other similar procedures, involving non-supine and non-motionless surgical site are total shoulder arthroplasty, ORIF shoulder procedure, patellar and quadriceps tendon ruptures, shoulder fractures with hemi replacement, Bankart repairs, and crush injuries affecting multiple tendons and digits of the hand and foot.

During these surgical procedures, the patient is often not in a supine position, and the joint is moved or exercised for soft tissue balancing during the surgery, before the muscles, tendons and nerves are reattached. During these surgical procedures, sutures are attached to the damaged or cut ends of muscles, tendons and nerves, hemostats are attached to the sutures and the surgeon grasps a handful of the hemostats to remove this material and open up the surgical site. During the procedure, the joint is manipulated, which can cause these sutures to become tangled and must be untangled to accurately balance the soft tissue. After the surgery is complete, the hemostats are again manually grasped to pull the ends together to balance the soft tissue; then these cut ends are reattached. Tangled sutures require extra, unneeded surgical staff time during the surgical procedure to untangle these sutures.

The prior art devices, the use of which is predicated on the patient being supine and motionless, are not adaptable to these joint and other surgeries, where motion of the surgical site is common, and where the patient is not usually supine.

There is a need for a clamp and/or suture retainer and organizer that is useful during joint surgery and other surgeries where the surgery site is not necessarily supine and where the surgery site may experience motion during the surgical procedure.

SUMMARY OF THE INVENTION

It is therefore an object of this invention to provide a suture and/or clamp retainer and organizer device which is useful during joint surgery and other surgeries where the patient is not necessarily supine and where the surgery site may experience motion during the surgical procedure. It is also an object of this invention to provide a holder for a plurality of suture hemostats, or clamps, to enhance the ability of the surgeon to balance and/or retract the soft tissue.

In one aspect, this invention features a suture clamp and/or suture device for use in surgery that involves movement of the surgery site during the surgical procedure, comprising an elongated body formed of resilient material and having a plurality of lateral slits through one surface thereof. The slits are sized to receive a surgical suture. The body includes a means adjacent each slit for receiving and retaining a hemostat attached to a suture.

In one embodiment each slit opens into a lateral passage through said body that is sized to receive and grip a hemostat. A tab, notch, surface or adhesive strips are provided to facilitate attachment of the body to a surgical drape or other supportive surface. In another embodiment the passage is a tapered pocket extending only partially through the body, and the slits and adjacent pockets are mounted in spaced pod mounted on a flexible strip.

These and other objects and features of this invention will become more readily apparent upon reference to the following detailed description of a preferred embodiment, as illustrated in the accompanying drawings, in which:

BRIEF DESCRIPTION OF THE DRAWINGS

FIG. 6 is a plan view of another embodiment of this invention;

FIG. 7 is a front view of the embodiment of FIG. 6;

FIG. 8 is a sectional view, taken along line C-C of FIG. 7;

FIG. 9 is a sectional view, taken along line B-B of FIG. 7; and

FIG. 10 is a perspective view of the FIGS. 6-9 embodiment, shown retaining two hemostats and attached sutures.

DESCRIPTION OF THE PREFERRED EMBODIMENT

Figure 1:
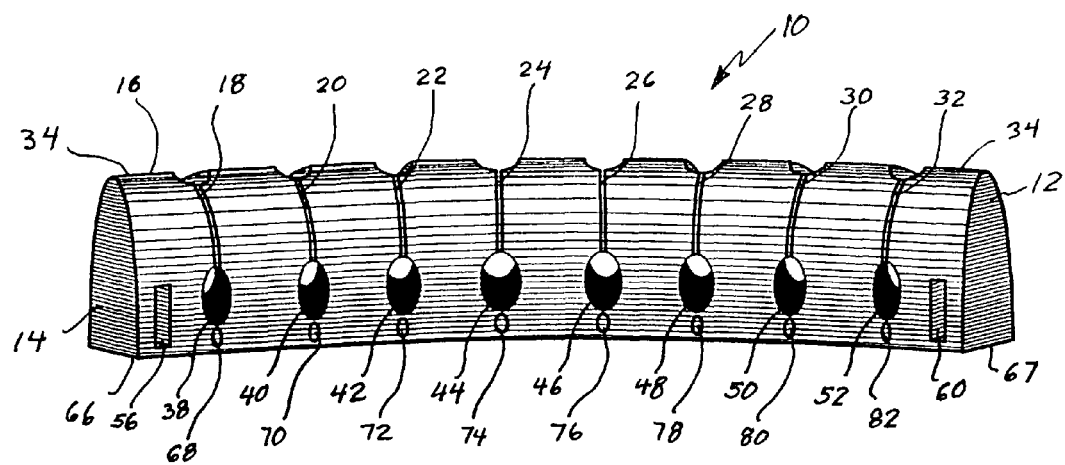
FIG. 1 is a front view of a suture and/or clamp retainer and organizer device according to this invention.
Figure 2:
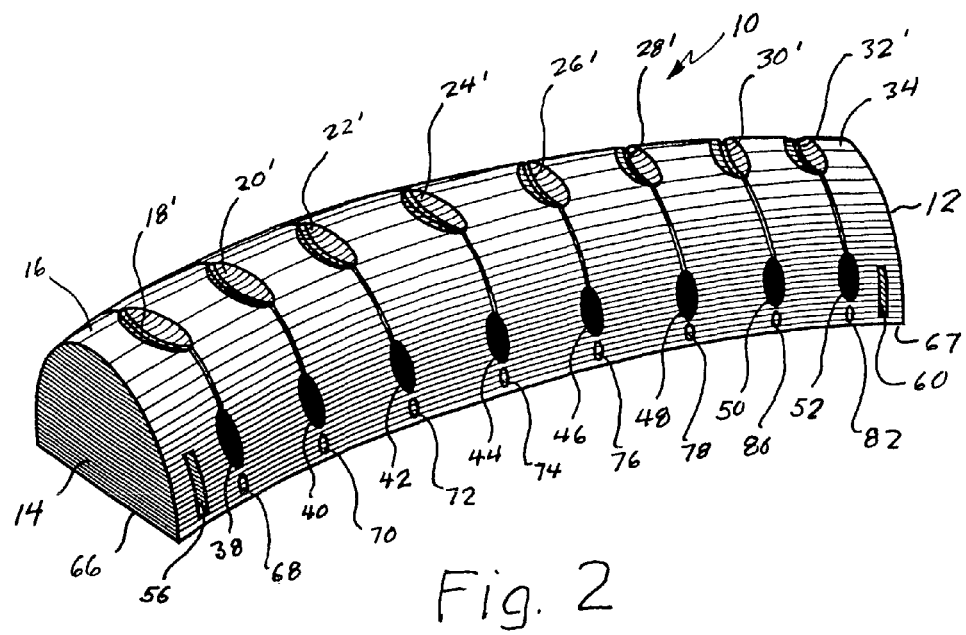
FIG. 2 is a perspective view of the device of FIG. 1.

As shown in FIGS. 1 and 2, a suture holder and organizer 10 comprises an elongated cruciform body 12 that is made of a resilient material, such as rubber, silicone or other plastic material. Body 12 has a semi-cylindrical cross-section and includes a flat base 14 and a curved upper surface 16. A plurality of lateral slits 18, 20, 22, 24, 26, 28, 30, 32 extend downwardly from the top 34 of upper surface 16 down through body 12. Each of the slits terminates in a through bore 38, 40, 42, 44, 46, 48, 50, 52, each of which tapers from a larger entry hole 38a, 40a, 42a, 44a, 46a, 48a, 50a, 52a, to a smaller exit hole.

At the body top 34, each slot is beveled at 18', 20', 22', 24', 26', 28', 30', 32'. A pair of slots 56, and 60 are formed adjacent each end of body 12. In addition, an adhesive strip can be mounted on bottom of base 14 at 66, 67 adjacent each end. Preparatory to surgery, several of the suture holders are attached to a surgical drape surrounding the surgical site by clamps which act through slot pairs 54, 56 and 58, 60 and/or by the adhesive strips.

Figure 3:
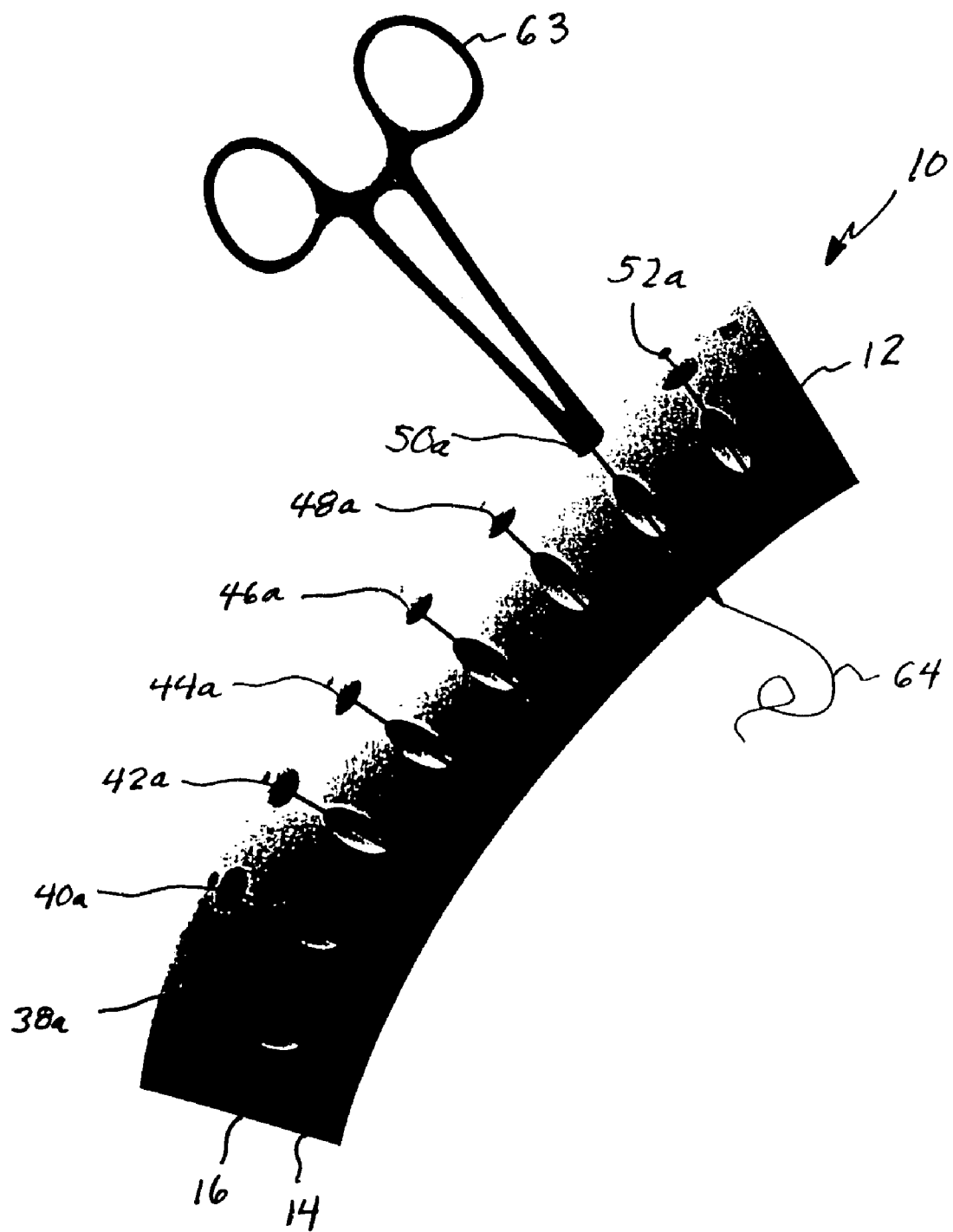
FIG. 3 is a perspective view of the device of FIGS. 1 and 2, shown holding a suture-clamping hemostat.

Referring now to FIG. 3, during surgery, a plurality of hemostats, exemplified here by hemostat 63 are attached to the ends of sutures, exemplified here by suture 64, that are attached to the ends of severed tendons, muscles and nerves (not illustrated) in a well-known manner. These hemostats are then used to insert the sutures into slots 18, 20, 22, 24, 26, 28, 30, 32, assisted by the beveled edges which guide the sutures into the slots. The hemostats are then inserted into through bores 38, 40, 42, 44, 46, 48, 50, 52, where they are securely gripped by the resilient material and held. The sutures are pulled tight to fully expose the surgery site by grasping holder 10 and pulling on it. In this manner, the surgeon is relieved of the necessity of untangling the sutures and grabbing a handful of hemostats to open the site or balance the tissue. Thus holder 10 both holds the hemostats and organizes the sutures to speed the surgical procedure and simplifying this aspect of the procedure for the surgeon.

As can be seen, hemostat 63 cannot be pulled fully through bore 50 because of its taper. When it is desired to reattach the soft tissue ends, hemostat 63 (and the others, not illustrated) is easily withdrawn back out the bore 50 to pull suture 64 back up and out of slot 30. Alternatively, the tip of hemostat 63 may wedge through slot 30 to remove suture 64. These actions are facilitated by the resilience of the silicone or other material of body 12.

To aid the surgeon in identifying sutures, identifying indicia, shown here as dots 68, 70, 72, 74, 76, 78, 80, 82, are placed on the surface 16 adjacent each bore near base 14. These indicia can be color coded, such as coloring the dots shown here, or alpha-numeric, comprising numbers or letters, which can be color-coded, or combinations of each.

Figure 4:
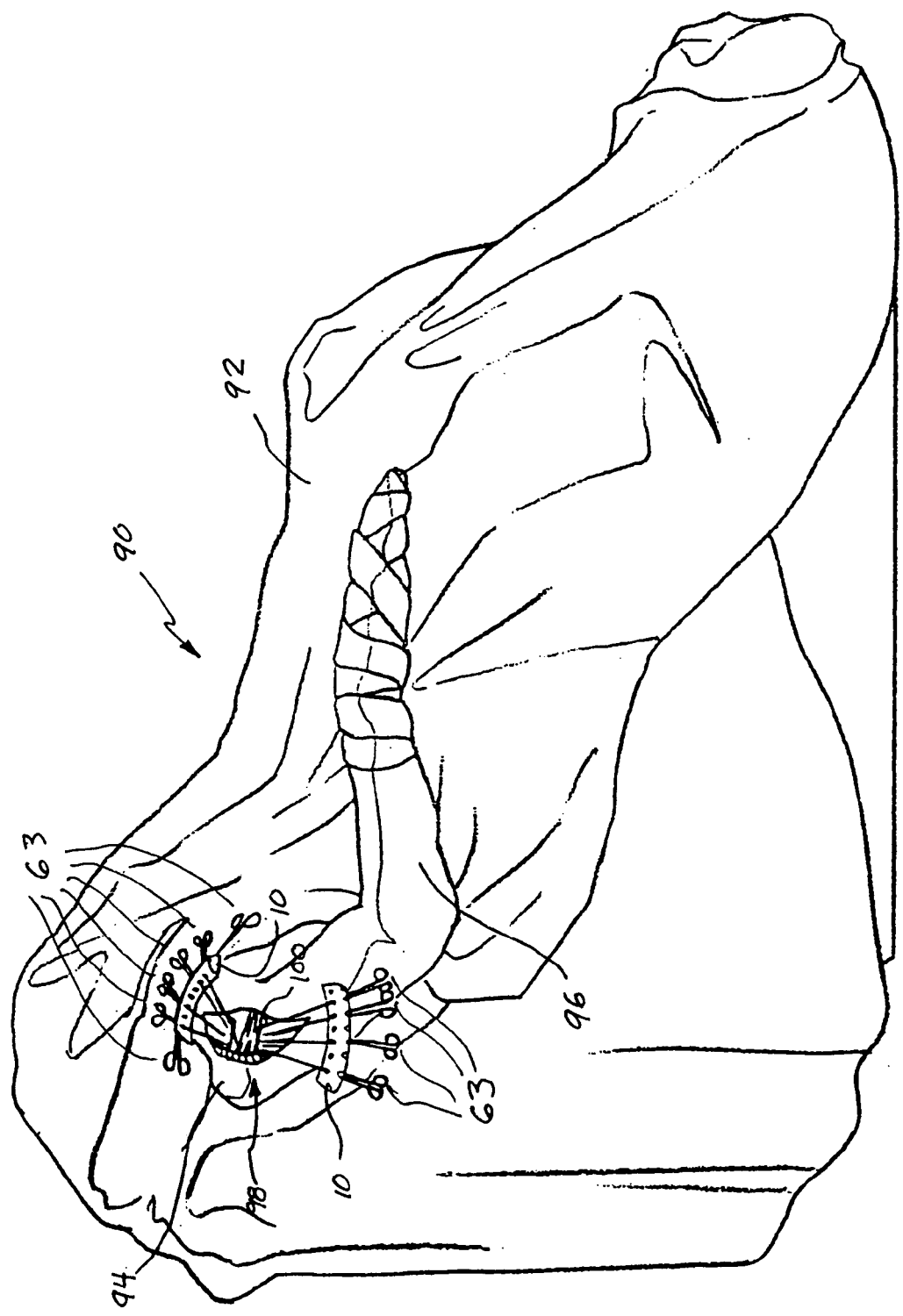
FIG. 4 is a perspective view of a shoulder surgery illustrating use of the device of this invention.
Figure 5:
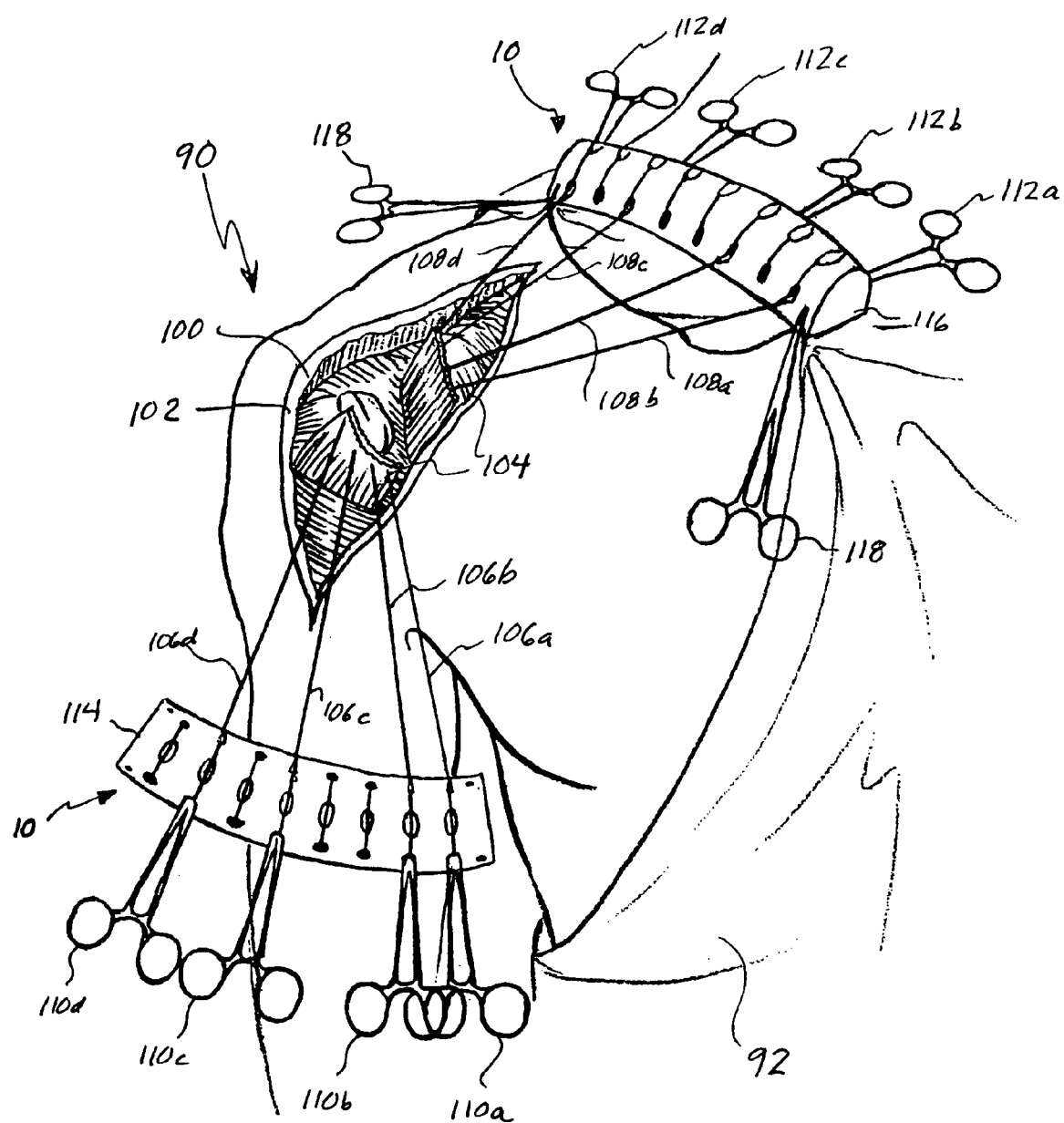
FIG. 5 is an enlarged partial view a portion of FIG. 4.

As illustrated in FIGS. 4 and 5, normally, multiple clamp and suture retainers and organizers 10 will be employed in an operation, preferably in identical pairs, as shown. In this manner, for example, sutures attached to the mating ends of a tendon can be placed in the same slots (e.g. "red" or "2-A") of each of the pair of suture holders. At the end of the surgery, identifying these mating sutures is quick and positive.

FIGS. 4 and 5 show a surgery patient 90, substantially covered by a surgical drape 92, with shoulder 94 of right arm 96 in the process of surgery at site 98. An incision 100 has exposed fat layer 102, and layers of various muscle groups, including the rotator cuff 104, which has been incised. Sutures 106 a, b, c, d and 108 a, b, c, d are attached to both of the severed ends of rotator cuff 104, and are gripped by respective hemostats 110, a, b, c, d and 112 a, b, c, d.

A pair of clamp and/or suture retainer and organizer devices 114 and 116. The upper device 116 is held to drape 92 by a pair of hemostats 118 to maintain tension on the sutures and to prevent dislodgement by patient movement or surgical action. In contrast, lower device 114 is left to hang, with gravity supplying the necessary tension. Note that the sutures cannot tangle and are held in any desired position as dictated by the surgeon (not shown). At surgery's end, the hemostats are removed from the devices, freeing the sutures for selective use by the surgeon.

Another embodiment of this invention is shown in FIGS. 6-10. Here, a clamp and/or suture retainer and organizer device 120 has a thin, elongated, flexible base 122 which mounts a plurality (here, 7 are shown) of egg-shaped pods 124, denominated on base 122 by embossed letters, a-h. Each pod 124 has a vertical through slit 126, which opens into a tapered pocket 128 for receiving the nose of a hemostat 130, as shown in FIG. 10. Each pod 124 includes a recess 132, which is adjacent to and opens into the slit 126. Recess 132 guides the nose of hemostat 130 as it slides suture 134 into slit 126. Pockets 128 closely grip and retain the nose of hemostat 130, but prevent it from being pulled through. The of base 122 provide a surface for enabling a hemostat to clamp device 120 onto a surgical drape, in the manner shown in FIGS. 4 and 5. Slits 126 are sufficiently narrower than the thickness of a suture to cause the walls to grip the sutures themselves, regardless of whether a hemostat is inserted into the adjacent recess 132. In this manner, the sutures themselves can be organized and retained.

Thus, use of this invention will simplify and facilitate uniform movement of sutures attached to soft tissue for retraction and/or balancing of the soft tissue during orthopedic surgeries, and may find use in other surgical procedures where suture clamping and organization are used.

While only a preferred embodiment has been described and shown, obvious modifications are contemplated within the scope of this invention, as defined by the appended claims. For example, the device could have different means for holding the hemostats, such as adhesive strips on the bottoms of the devices. Any sterilizable flexible material, such as "C-Flex" can be utilized.

The invention claimed is:

1. A suture clamp and/or suture retainer and organizer device for use during a surgical procedure, comprising an elongated body formed of resilient material and having a plurality of lateral slits through one surface thereof, said slits being sized to receive and grip a surgical suture, pocket means adjacent each slit for receiving and retaining a hemostat attached to a suture against being pulled through the body, and attachment means for facilitating attachment of the body to a surgical drape or other supportive surface.

2. The device of claim 1, wherein the pocket means adjacent each slit comprise a tapered pocket extending into the body to retain a hemostat in the pocket and prevent the hemostat from being pulled through the body.

3. The device of claim 2, including unique indicia means located in the body adjacent each slit and pocket for identifying each such slit and lateral passage, said indicia means being alpha-numeric or colored marks.

4. The device of claim 1, wherein the body has an elongated cruciform shape, and a semi-cylindrical cross-section.

5. The device of claim 1, wherein the body comprises a flexible elongated base having a plurality of spaced pods mounted thereon, with a slit and adjacent pocket being located in each pod.

6. The suture organizer of claim 5, wherein the pods are beveled on the surface to facilitate movement of sutures into the slits, and the slits are narrower than the thickness of a suture.

7. The device of claim 1, wherein the body is made of a sterilizable material.

* * * * *